(12) United States Patent
Gobbi et al.

(10) Patent No.: US 7,268,154 B2
(45) Date of Patent: Sep. 11, 2007

(54) SUBSTITUTED TRIAZOLE COMPOUNDS

(75) Inventors: Luca Claudio Gobbi, Oberwil (CH); Marius Hoener, Basel (CH); Claus Riemer, Freiburg (DE); Will Spooren, Franken (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/488,837

(22) Filed: Jul. 18, 2006

(65) Prior Publication Data

US 2007/0021475 A1    Jan. 25, 2007

(30) Foreign Application Priority Data

Jul. 25, 2005   (EP)   ................... 05106802

(51) Int. Cl.
A61K 31/4192   (2006.01)
A61K 31/454    (2006.01)
C07D 249/04    (2006.01)
C07D 401/06    (2006.01)

(52) U.S. Cl. ...................... 514/359; 514/326; 548/255; 546/210

(58) Field of Classification Search ................ 548/255; 546/210; 514/359, 326
See application file for complete search history.

(56) References Cited

FOREIGN PATENT DOCUMENTS

WO   WO 2005/000821 A1   1/2005
WO   WO 2005/014575 A1   2/2005

OTHER PUBLICATIONS

Tooney et al., Neurosci. Letters, 2000, vol. 283, pp. 185-188.
Giardina et al., Exp. Opin. Ther. Patents, 2000, vol. 10, pp. 939-960.
Jung et al., Neuroscience, 1996, vol. 74, pp. 403-414.
Höllt et al., Neuropeptides, 1998, vol. 5, pp. 481-484.
Stoessl et al., 1989, Neurosci. Letters, 1987, vol. 80(3), pp. 321-326.
Millan et al., Psychopharmacology, vol. 14, 2000, pp. 114-138.
Panocka et al., Peptides, 2001, vol. 22(7) pp. 1037-1042.
Ribeiro et al., Neurosci. Letters, 1998, vol. 258(3) pp. 155-158.
Knapp et al., Br J. Psychiatry, 2002, vol. 180, pp. 19-23.
Kameyama et al., Methods Find Exp Clin Pharmacol. 1998, vol. 20(7), pp. 555-560.
Noguchi, et al., Heterocycles, 2002, vol. 58, pp. 471-504.
Kanner, et al., Tetrahedron, 1982, vol. 38(24), pp. 3597-3604.

*Primary Examiner*—Rebecca Anderson
*Assistant Examiner*—Karen Cheng
(74) *Attorney, Agent, or Firm*—George W. Johnston; Patricia S. Rocha-Tramaloni; Kimberly J. Prior

(57) ABSTRACT

The present invention relates to compounds of formula (I)

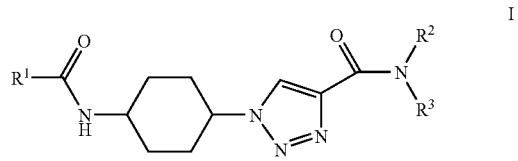

wherein
$R^1$, $R^2$ and $R^3$ are as defined in the specification and to pharmaceutically suitable acid addition salts thereof. The invention includes all sterioisomeric forms, including individual diastereoisomers and enantiomers of the compound of formula (I) as well as racemic and non-racemic mixtures thereof. It has been found that the present compounds are selective allosteric positive modulators of the human NK-3 receptor for the treatment of anxiety, depression, bipolar disorders, Parkinson's disease, schizophrenia and pain.

62 Claims, No Drawings

SUBSTITUTED TRIAZOLE COMPOUNDS

PRIORITY TO RELATED APPLICATIONS

This application claims the benefit of European Application No. 05106802.1, filed Jul. 25, 2005, which is hereby incorporated by reference in its entirety.

BACKGROUND OF THE INVENTION

The three main mammalian tachykinins, substance P (SP), neurokinin A(NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters*, 2000, 283, 185-188; *Exp. Opin. Ther. Patents* 2000, 10, 939-960; *Neuroscience*, 1996, 74, 403-414; *Neuropeptides*, 1998, 32, 481-488).

Neurokinin 3 receptors are expressed in the brain and strategically located along with NKB, i.e. its natural substrate, in noradrenergic and dopaminergic pathways. Indeed, CNS administration of senktide, a peptide agonist of NK-3 receptors, increases noradrenaline and dopamine in brain areas such as the prefrontal cortex. NK-3 receptors are less abundant in serotonergic pathways, nevertheless, intracerebroventricular administration of senktide elicits behavioural manifestations of serotonergic stimulation, such as forepaw treading, that were blocked by serotonin depletion (Stoessl et al., 1989, *Neurosci. Letters*, 1987, 80(3), 321-6).

Thus, activation of NK-3 receptors stimulates noradrenergic, dopaminergic and serotonergic systems, i.e., those that are critically involved in the anti-depressant and anxiolytic effects of SSRI's (serotonin re-uptake inhibitors) and SNRI's (serotonin noradrenaline re-uptake inhibitors (Millan et al., *Psychopharmacoogy* 14 (2000), 114-138). Indeed, preliminary mice studies suggest that intraperitoneal administration of the NK-3 agonist aminosenktide exhibits anti-depressant-like effects in the forced swimming test (Panocka et al, *Peptides*, 2001, 22(7), 1037-42), and that intracerebroventricular administration of senktide exhibits anxiolytic-like effects in the elevated plus maze (Ribeiro and De Lima, *Neurosci Letters*, 1998, 258(3), 155-8).

In addition, because cognitive impairment may be an important element of these diseases (Knapp et al., *Br J Psychiatry*, 2002, 18, 19-23), it is of great interest that senktide, after its local administration in the area of cholinergic cell bodies (septal area) stimulates acetylcholine in the hippocampus. Indeed, senktide ameliorates the scopolamine-induced impairment in a cognition test (Kameyama et al., *Methods Find Exp Clin Pharmacol*, 1998, 20(7), 555-60).

In conclusion, based on biochemical and behavioral data, activation of NK-3 receptors is expected to lead to anti-depressant and anxiolytic-like effects, and in addition, to ameliorate possible cognitive deficits for the treatment of anxiety, depression, bipolar disorders, Parkinson's disease, schizophrenia and pain.

SUMMARY OF THE INVENTION

The present invention provides compounds of formula (I)

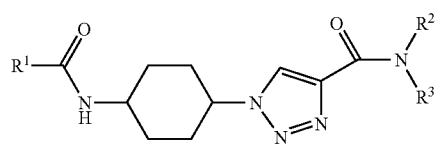

wherein
R$^1$ is —(CRR')$_n$-aryl, —(CRR')$_n$-heteroaryl, —(CRR')$_n$—O-aryl or —(CRR')$_n$—O-heteroaryl, wherein the aryl or heteroaryl groups are unsubstituted or substituted by one or two substituents selected from the group consisting of halogen, lower alkyl, lower alkoxy, lower alkyl substituted by halogen, and unsubstituted or substituted phenyl, wherein the substitution on the phenyl group is lower alkyl or halogen, or is —(CRR')$_n$-2-benzo[1.3]dioxolyl;
R and R' are each independently selected from hydrogen and lower alkyl or are together with the carbon atom to which they are attached a cycloalkyl group;
R$^2$ and R$^3$ are each independently selected from hydrogen, lower alkyl, phenyl or cycloalkyl or together with the N-atom to which they are attached form a five or six membered saturated heterocycle;
n is 0 or 1;

and pharmaceutically suitable acid addition salts thereof.

The invention includes all sterioisomeric forms, including individual diastereoisomers and enantiomers of the compound of formula (I) as well as racemic and non-racemic mixtures thereof.

The invention also provides pharmaceutical compositions containing the compounds of the invention and a pharmaceutically acceptable carrier as well as processes for preparation of such compounds and compositions.

Compounds of the invention are selective allosteric positive modulators of the human NK-3 receptor. The invention further provides methods for the treatment of anxiety, depression, bipolar disorders, Parkinson's disease, schizophrenia and pain.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like. Preferred lower alkyl groups are groups with 1-4 carbon atoms.

The term "lower alkoxy" denotes a group containing an alkyl residue as defined above, and which is attached via an oxygen atom.

The term "halogen" denotes chlorine, iodine, fluorine and bromine.

The term "cycloalkyl" denotes a saturated carbocyclic group containing 3-6 carbon atoms.

The term "aryl" denotes a cyclic aromatic hydrocarbon radical consisting of one or more fused rings in which at least one ring is aromatic in nature, for example phenyl, benzyl, naphthyl or indanyl. Preferred is the phenyl group.

The term "heteroaryl" denotes a cyclic aromatic hydrocarbon radical consisting of one or more fused rings in which at least one ring is aromatic in nature, and which contains at least one heteroatom, selected from N, O and S, for example pyridyl, pyrimidyl, oxadiazolyl, triazolyl, tetrazolyl, thiazolyl, thienyl, furyl or imidazolyl. The preferred heteroaryl group is pyridyl.

The term "five or six membered saturated heterocycle" denotes a saturated carbocyclic ring having five or six ring members in which at least one ring member is selected from N, O and S, for example, pyrrolidin-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl. Preferred heterocyclic groups are pyrrolidin-1-yl or piperidin-1-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The following groups of compounds of formula (I) are preferred:

"Therapeutically effective amount" means an amount that is effective to prevent, alleviate or ameliorate symptoms of disease or prolong the survival of the subject being treated.

The present invention provides compounds of formula (I)

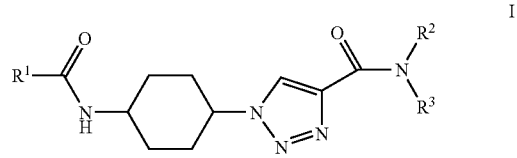

I wherein
$R^1$ is —$(CRR')_n$-aryl, —$(CRR')_n$-heteroaryl, —$(CRR')_n$—O-aryl or —$(CRR')_n$—O-heteroaryl, wherein the aryl or heteroaryl groups are unsubstituted or substituted by one or two substituents selected from the group consisting of halogen, lower alkyl, lower alkoxy, lower alkyl substituted by halogen, and unsubstituted or substituted phenyl, wherein the substitution on the phenyl group is lower alkyl or halogen, or is —$(CRR')_n$-2-benzo[1.3]dioxolyl;
R and R' are each independently selected from hydrogen and lower alkyl or are together with the carbon atom to which they are attached a cycloalkyl group;
$R^2$ and $R^3$ are each independently selected from hydrogen, lower alkyl, phenyl or cycloalkyl or together with the N-atom to which they are attached form a five or six membered saturated heterocycle;
n is 0 or 1;

and pharmaceutically suitable acid addition salts thereof.

In one embodiment, the invention provides compounds of formula I in which $R^1$ is $(CRR')_n$-aryl which is optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen. Within this embodiment are compounds, in which $R^1$ is —$CH_2$-phenyl, wherein the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

The following compounds relate to this group
2-(2-chloro-6-fluoro-phenyl)-N-{cis-4-[4-(pyrrolidine-1-carbonyl)-[1,2,3]triazol-1-yl]-cyclohexyl}-acetamide,
1-{cis-4-[2-(2-chloro-6-fluoro-phenyl)-acetylamino]-cyclohexyl}-1H-[1,2,3]triazole-4-carboxylic acid phenylamide,
1-{cis-4-[2-(2-chloro-6-fluoro-phenyl)-acetylamino]-cyclohexyl}-1H-[1,2,3]triazole-4-carboxylic acid cyclopentylamide,
2-(2-chloro-6-fluoro-phenyl)-N-{cis-4-[4-(piperidine-1-carbonyl)-[1,2,3]triazol-1-yl]-cyclohexyl}-acetamide and
1-{cis-4-[2-(2-chloro-6-fluoro-phenyl)-acetylamino]-cyclohexyl}-1H-[1,2,3]triazole-4-carboxylic acid diethylamide.

Also within this embodiment are compounds, in which $R^1$ is phenyl and the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

The following compounds relate to this group
3'-methyl-biphenyl-3-carboxylic acid {cis-4-[4-(pyrrolidine-1-carbonyl)-[1,2,3]triazol-1-yl]-cyclohexyl}-amide,
4'-fluoro-biphenyl-3-carboxylic acid {cis-4-[4-(pyrrolidine-1-carbonyl)-[1,2,3]triazol-1-yl]-cyclohexyl}-amide,
2-methoxy-N-{cis-4-[4-(pyrrolidine-1-carbonyl)-[1,2,3]triazol-1-yl]-cyclohexyl}-benzamide,
3,4-dimethoxy-N-{cis-4-[4-(pyrrolidine-1-carbonyl)-[1,2,3]triazol-1-yl]-cyclohexyl}-benzamide
4-methoxy-N-{cis-4-[4-(pyrrolidine-1-carbonyl)-[1,2,3]triazol-1-yl]-cyclohexyl}-benzamide,
4-chloro-N-{cis-4-[4-(pyrrolidine-1-carbonyl)-[1,2,3]triazol-1-yl]-cyclohexyl}-benzamide,
3-chloro-N-{cis-4-[4-(pyrrolidine-1-carbonyl)-[1,2,3]triazol-1-yl]-cyclohexyl}-benzamide,
3-fluoro-N-{cis-4-[4-(pyrrolidine-1-carbonyl)-[1,2,3]triazol-1-yl]-cyclohexyl}-benzamide,
2-fluoro-N-{cis-4-[4-(pyrrolidine-1-carbonyl)-[1,2,3]triazol-1-yl]-cyclohexyl}-benzamide,
2-chloro-N-{cis-4-[4-(pyrrolidine-1-carbonyl)-[1,2,3]triazol-1-yl]-cyclohexyl}-benzamide,
4-fluoro-N-{cis-4-[4-(pyrrolidine-1-carbonyl)-[1,2,3]triazol-1-yl]-cyclohexyl}-benzamide and
N-{cis-4-[4-(pyrrolidine-1-carbonyl)-[1,2,3]triazol-1-yl]-cyclohexyl}-benzamide.

Also within this embodiment are compounds in which $R^2$ and $R^3$ are each independently hydrogen or lower alkyl. Alternatively, compounds in this embodiment are those wherein at least one of $R^2$ and $R^3$ is cycloalkyl. Other such compounds are those in which at least one of $R^2$ and $R^3$ is phenyl. Still other such compounds are those in which $R^2$ and $R^3$ together with the N-atom to which they are attached form a five or six membered saturated heterocycle.

In another embodiment, the invention provides compounds of formula I in which $R^1$ is $(CRR')_n$—O-aryl which is optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen. Within this embodiment are compounds, wherein $R^1$ is —CH(CH$_3$)—O-phenyl, wherein the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

The following compound relates to this group
2-(4-chloro-2-methyl-phenoxy)-N-{cis-4-[4-(pyrrolidine-1-carbonyl)-[1,2,3]triazol-1-yl]-cyclohexyl}-propionamide.

Also within this embodiment are compounds in which $R^2$ and $R^3$ are each independently hydrogen or lower alkyl. Alternatively, compounds in this embodiment are those wherein at least one of $R^2$ and $R^3$ is cycloalkyl. Other such compounds are those in which at least one of $R^2$ and $R^3$ is phenyl. Still other such compounds are those in which $R^2$ and $R^3$ together with the N-atom to which they are attached form a five or six membered saturated heterocycle.

In another embodiment, the invention provides compounds of formula I in which $R^1$ is (CRR')$_n$-2-benzo[1.3]dioxolyl. Within this embodiment are compounds, wherein $R^1$ is —CH$_2$-2-benzo[1.3]dioxolyl.

The following compound relates to this group
2-benzo[1,3]dioxol-5-yl-N-{cis-4-[4-(pyrrolidine-1-carbonyl)-[1,2,3]triazol-1-yl]-cyclohexyl}-acetamide.

Also within this embodiment are compounds where $R^1$ is 2-benzo[1.3]dioxolyl.

The following compound relates to this group
benzo[1,3]dioxole-5-carboxylic acid {cis-4-[4-(pyrrolidine-1-carbonyl)-[1,2,3]triazol-1-yl]-cyclohexyl}-amide.

Also within this embodiment are compounds in which $R^2$ and $R^3$ are each independently hydrogen or lower alkyl. Alternatively, compounds in this embodiment are those wherein at least one of $R^2$ and $R^3$ is cycloalkyl. Other such compounds are those in which at least one of $R^2$ and $R^3$ is phenyl. Still other such compounds are those in which $R^2$ and $R^3$ together with the N-atom to which they are attached form a five or six membered saturated heterocycle.

In another embodiment, the invention provides compounds of formula I in which $R^{1'}$ is (CRR')$_n$-heteroaryl which is optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen. Within this embodiment are compounds, wherein $R^1$ is pyridinyl.

The following compound relates to this group
N-{cis-4-[4-(pyrrolidine-1-carbonyl)-[1,2,3]triazol-1-yl]-cyclohexyl}-6-trifluoromethyl-nicotinamide.

Also within this embodiment are compounds in which $R^2$ and $R^3$ are each independently hydrogen or lower alkyl. Alternatively, compounds in this embodiment are those wherein at least one of $R^2$ and $R^3$ is cycloalkyl. Other such compounds are those in which at least one of $R^2$ and $R^3$ is phenyl. Still other such compounds are those in which $R^2$ and $R^3$ together with the N-atom to which they are attached form a five or six membered saturated heterocycle.

The invention also provides compounds, in which $R^1$ is —C(R,R')-phenyl, and the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen and R and R' are together with the carbon atom to which they are attached a cycloalkyl group.

The following compound relates to this group
1-(2-chloro-6-fluoro-phenyl)-cyclopentanecarboxylic acid {cis-4-[4-(pyrrolidine-1-carbonyl)-[1,2,3]triazol-1-yl]-cyclohexyl}-amide.

The invention further provides compounds in which $R^1$ is (CRR')$_n$—O-heteroaryl which is optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen. Within this embodiment are compounds in which $R^2$ and $R^3$ are each independently hydrogen or lower alkyl. Alternatively, compounds in this embodiment are those wherein at least one of $R^2$ and $R^3$ is cycloalkyl. Other such compounds are those in which at least one of $R^2$ and $R^3$ is phenyl. Still other such compounds are those in which $R^2$ and $R^3$ together with the N-atom to which they are attached form a five or six membered saturated heterocycle.

In another embodiment, the invention provides compounds of formula I wherein $R^2$ and $R^3$ form together with the N-atom to which they are attached a five or six membered saturated heterocycle, in particular a pyrrolidine or piperidine ring. Among these compounds are those in which $R^1$ is (CRR')$_n$-aryl. Alternatively, this embodiment includes compounds in which $R^1$ is (CRR')$_n$—O-aryl. Also among these compounds are those in which $R^1$ is (CRR')$_n$-heteroaryl. Further compounds within this embodiment are those in which $R^1$ is (CRR')$_n$—O-heteroaryl. In each of these compounds, the aryl or heteroaryl group is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

In another embodiment, the invention provides compounds of formula I wherein $R^3$ is phenyl. Among these compounds are those in which $R^1$ is (CRR')$_n$-aryl. Alternatively, this embodiment includes compounds in which $R^1$ is (CRR')$_n$—O-aryl. Also among these compounds are those in which $R^1$ is (CRR')$_n$-heteroaryl. Further compounds within this embodiment are those in which $R^1$ is (CRR')$_n$—O-heteroaryl. In each of these compounds, the aryl or heteroaryl group is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

In another embodiment, the invention provides compounds of formula I in which $R^3$ is cycloalkyl. Among these compounds are those in which $R^1$ is (CRR')$_n$-aryl. Alternatively, this embodiment includes compounds in which $R^1$ is (CRR')$_n$—O-aryl. Also among these compounds are those in which $R^1$ is (CRR')$_n$-heteroaryl. Further compounds within this embodiment are those in which $R^1$ is (CRR')$_n$—O-heteroaryl. In each of these compounds, the aryl or heteroaryl group is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

In yet another embodiment, the invention provides compounds of formula I in which $R^2$ and $R^3$ are each independently lower alkyl. Among these compounds are those in which $R^1$ is $(CRR')_n$-aryl. Alternatively, this embodiment includes compounds in which $R^1$ is $(CRR')_n$—O-aryl. Also among these compounds are those in which $R^1$ is $(CRR')_n$-heteroaryl. Further compounds within this embodiment are those in which $R^1$ is $(CRR')_n$—O-heteroaryl. In each of these compounds, the aryl or heteroaryl group is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

Compounds, wherein $R^2$ and $R^3$ are independently from each other hydrogen, lower alkyl, phenyl or cycloalkyl.

The compounds of formula I of the present invention can be prepared by processes, which processes comprise a) coupling a pharmaceutically acceptable salt of an amine of formula (II)

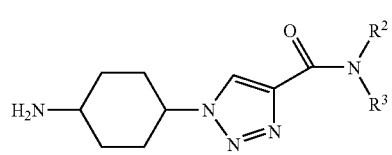

II with a carboxylic acid of formula (III)

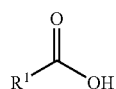

III to obtain a compound of formula (I)

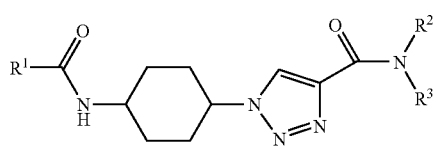

I or
b) reacting a compound of formula (IV)

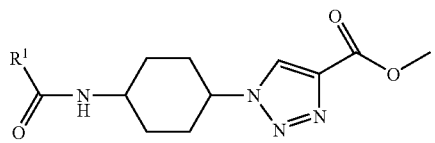

IV with an amine of formula (V)

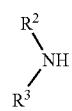

V to obtain a compound of formula (I)

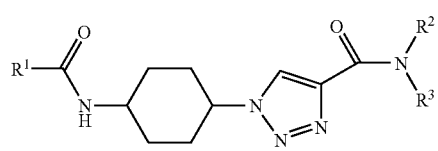

I or
c) reacting a compound of formula (VI)

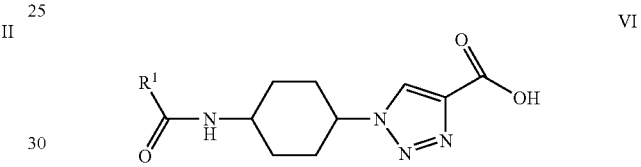

VI with an amine of formula (V)

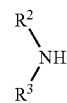

V to obtain a compound of formula (I)

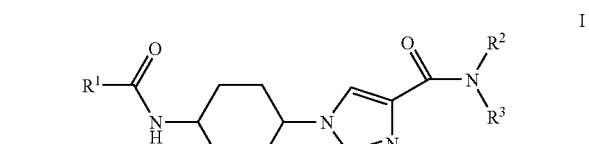

I wherein $R^1$-$R^3$ are as described above, and, if desired, converting a compound of formula (I) obtained into pharmaceutically active acid addition salts.

In accordance with process step a), a compound of formula (I) can be prepared by reacting a compound of formula (II) with a compound of formula (III) in the presence of a coupling reagent such as 2-(1H-benzotriazole-1-yl)-1,1,3,3-tetramethyluronium tetrafluoroborate and a base such as N,N-diisopropylethylamine in a solvent such as DMF, or alternatively, compounds of formula (I) can be prepared from a methyl ester of formula (IV) and an amine of formula (V) by reaction with a reagent such as $Me_3Al$ in a solvent such as toluene at about 0° C., or alternatively compounds of formula (I) can be prepared reacting a carboxylic acid of formula (VI) with an amine of formula (V) in the presence of a coupling reagent such as 2-(1H-benzotriazole-1-yl)-1,1,3,3-tetramethyluronium tetrafluoroborate and a base such as N,N-diisopropylethylamine in a solvent such as DMF.

In more detail, compounds of formula (I) can be prepared according to schemes 1, 2 and 3.

The following abbreviations have been used in the schemes:
DPPA=diphenylphosphoryl azide
DEAD=dimethyl azodicarboxylate
THF=tetrahydrofurane;
TBTU=2-(1H-benzotriazole-1-yl)-1,1,3,3-tetramethyluronium tetrafluoroborate
DMF=N,N-dimethylformamide;

The starting materials are known compounds or can be prepared by methods known in the art.

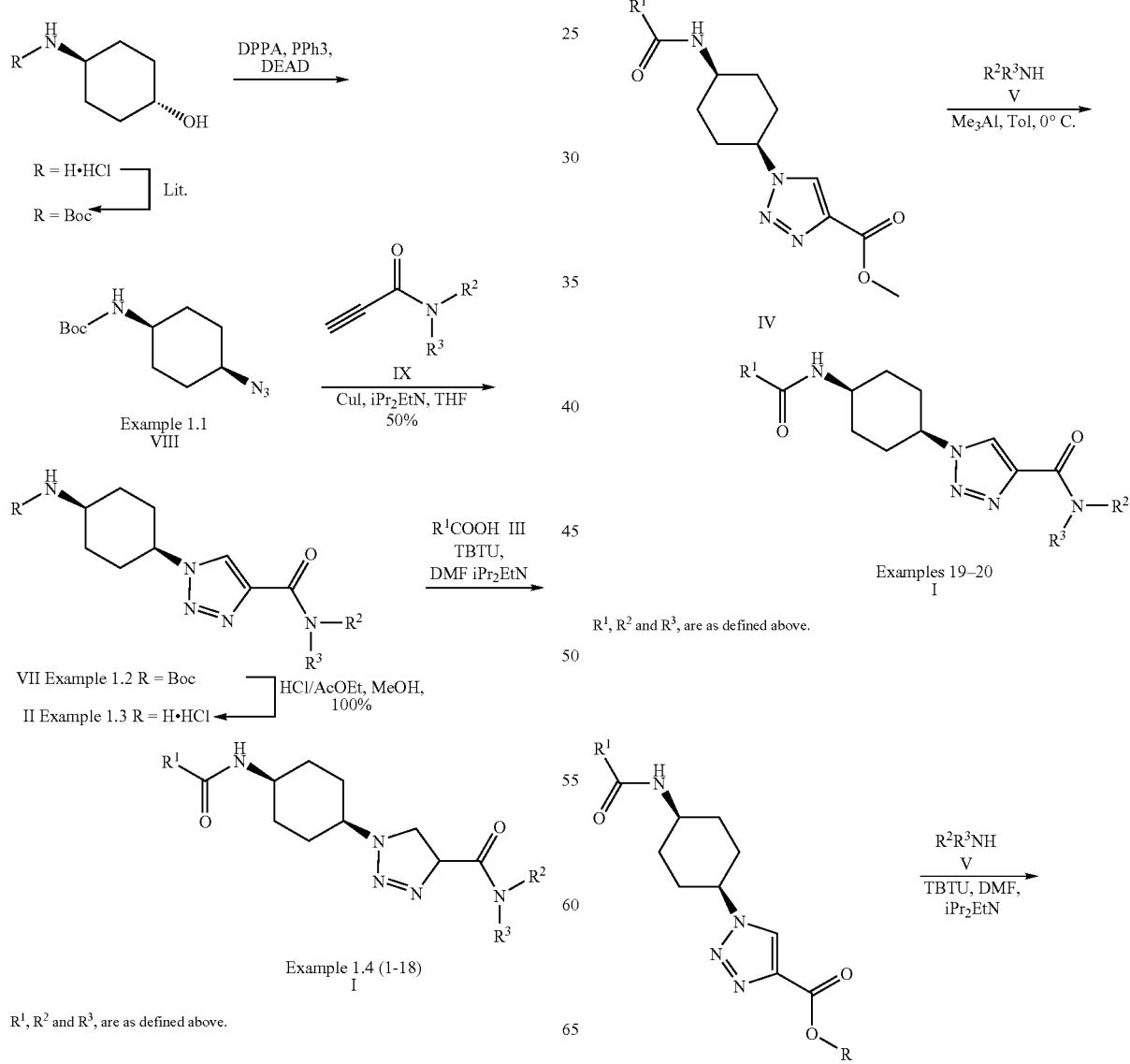

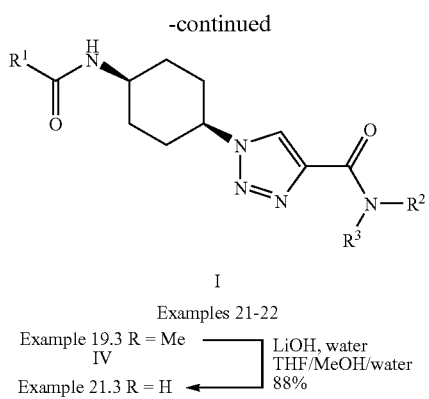

Examples 21-22

Example 19.3 R = Me ⟶ LiOH, water THF/MeOH/water 88%
IV
Example 21.3 R = H ⟵
VI $R^1$, $R^2$ and $R^3$ are as defined above.

An amine of formula (II) can be obtained by the treatment of a compound of formula (VII) with an acid such as HCl in a mixture of solvents such as EtOAc and MeOH.

Scheme 1

Compounds of formula (VII) can be obtained by reacting an azide of formula (VIII) with an acetylene of formula (IX) in the presence of a copper (I) reagent, such as CuI, and of a base, such as N,N-diisopropylethylamine, in a solvent, such as THF.

Azide (VIII) can be prepared from (trans-4-hydroxy-cyclohexyl)carbamic acid tert-butyl ester by methods known in the art. For example, the reaction can be performed with $PPh_3$, diethyl azodicarboxylate and diphenylphosphoryl azide in a solvent, such as THF, at about −10° C.

Scheme 2

A methyl ester of formula (IV) is obtained by coupling any pharmaceutically acceptable salt of an amine such as (X) and a carboxylic acid of formula (III) with methods known in the art. For example, the reaction can be performed with 2-(1H-benzotriazole-1-yl)-1,1,3,3-tetramethyluronium tetrafluoroborate and a base, such as N,N-diisopropylethylamine, in a solvent, such as DMF.

An amine of formula (X) can be obtained by the treatment of a carbamate of formula (XI) with an acid, such HCl, in a mixture of solvents, such as EtOAc/MeOH.

A compound of formula (XI) can be prepared from an azide, such as (VIII), by reaction with propiolic acid methyl ester in the presence of a copper (I) reagent, such as CuI, and of a base, such as N,N-diisopropylethylamine, in a solvent, such as THF.

Scheme 3

A carboxylic acid of formula (VI) can be prepared from a methyl ester of formula (IV) by treatment with a base, such as LiOH, in a solvent mixture, such as THF/MeOH/$H_2O$.

Salt formation is effected at room temperature in accordance with methods that are known per se and which are familiar to a person skilled in the art. Not only salts with inorganic acids, but also salts with organic acids are contemplated by the invention. Hydrochlorides, hydrobromides, sulphates, nitrates, citrates, acetates, maleates, succinates, methan-sulphonates, p-toluenesulphonates and the like are examples of such salts.

As mentioned earlier, the compounds of formula I and their pharmaceutically usable addition salts possess valuable pharmacological properties. Compounds of the present invention are allosteric positive modulators of neurokinin 3 (NK-3) receptors.

The compounds were investigated in accordance with the tests given hereinafter.

Test Description:

Calcium mobilization assay: HEK293 stably expressing NK3 were seeded at a density of 50,000 cells into poly-D-lysine coated 96-well blackwall, clear-bottom microtiter plates (Becton Dickinson Labware, Bedford, Mass.). One day later, the medium was removed, and 100 μl loading medium [HBSS without phenol red, supplemented with 20 mM HEPES-acid, and 2 μM Fluo-4AM solubilized in 0.5 mM Pluronic F-127/DMSO (Molecular Probes, Leiden, The Netherlands)] was added. Cells were loaded for 1 h at 37° C., washed twice with 150 μl assay buffer (loading buffer without Fluo-4 AM), and then 260 μl assay buffer was added. Cells were further pre-incubated at room temperature before adding the agonist Neurokinin B with or without enhancer in 50 μl assay buffer and then measured on a T-channel fluorimetric imaging plate reader (FLIPR, Molecular Devices, Sunnyvale, Calif.). Maximum change in fluorescence over baseline was used to determine agonist response.

The efficacy as allosteric positive modulators of neurokinin 3 (NK-3) receptors is given in the table below as $EC_{50}$ and fold increase of the Neurokinin B agonistic effect. The $EC_{50}$ of preferred compounds is <5.0 μM.

| Example | Compound name | $EC_{50}$ [μM] (fold increase) |
|---|---|---|
| 1 | 2-(2-Chloro-6-fluoro-phenyl)-N-{cis-4-[4-(pyrrolidine-1-carbonyl)-[1,2,3]triazol-1-yl]-cyclohexyl}-acetamide | 3.7 (2.3) |
| 2 | 3'-Methyl-biphenyl-3-carboxylic acid {cis-4-[4-(pyrrolidine-1-carbonyl)-[1,2,3]triazol-1-yl]-cyclohexyl}-amide | 0.20 (1.5) |
| 3 | 4'-Fluoro-biphenyl-3-carboxylic acid {cis-4-[4-(pyrrolidine-1-carbonyl)-[1,2,3]triazol-1-yl]-cyclohexyl}-amide | 0.86 (1.6) |
| 4 | 2-(4-Chloro-2-methyl-phenoxy)-N-{cis-4-[4-(pyrrolidine-1-carbonyl)-[1,2,3]triazol-1-yl]-cyclohexyl}-propionamide | 0.56 (1.7) |
| 6 | 2-Methoxy-N-{cis-4-[4-(pyrrolidine-1-carbonyl)-[1,2,3]triazol-1-yl]-cyclohexyl}-benzamide | 4.2 (3.2) |
| 7 | 3,4-Dimethoxy-N-{cis-4-[4-(pyrrolidine-1-carbonyl)-[1,2,3]triazol-1-yl]-cyclohexyl}-benzamide | 4.5 (5.6) |
| 9 | 4-Chloro-N-{cis-4-[4-(pyrrolidine-1-carbonyl)-[1,2,3]triazol-1-yl]-cyclohexyl}-benzamide | 2.3 (2.2) |
| 17 | 1-(2-Chloro-6-fluoro-phenyl)-cyclopentanecarboxylic acid {cis-4-[4-(pyrrolidine-1-carbonyl)-[1,2,3]triazol-1-yl]-cyclohexyl}-amide | 0.77 (1.8) |
| 19 | 1-{cis-4-[2-(2-Chloro-6-fluoro-phenyl)-acetylamino]-cyclohexyl}-1H-[1,2,3]triazole-4-carboxylic acid phenylamide | 1.8 (1.6) |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the invention are selective allosteric positive modulators of the human NK-3 receptor. The invention further provides methods for the treatment of anxiety, depression, bipolar disorders, Parkinson's disease, schizophrenia and pain.

The compounds and compositions of the invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention can be administered rectally, for example, in the form of suppositories or parenterally, for example, in the form of injectable solutions.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention without limiting it. All temperatures are given in degrees Celsius.

Abbreviations

DIPEA=N,N-diisopropylethylamine;

DMF=N,N-dimethylformamide;

MS=mass spectroscopy;

RT=room temperature;

TBTU=2-(1H-benzotriazole-1-yl)-1,1,3,3-tetramethyluronium tetrafluoroborate;

THF=tetrahydrofurane;

Tol=toluene.

EXAMPLE 1

2-(2-Chloro-6-fluoro-phenyl)-N-{cis-4-[4-(pyrrolidine-1-carbonyl)-[1,2,3]triazol-1-yl]-cyclohexyl}-acetamide 1.1 (cis-4-Azido-cyclohexyl)carbamic acid tert-butyl ester To a cooled (−10° C.) and stirred solution under Ar of (trans-4-hydroxy-cyclohexyl)carbamic acid tert-butyl ester (10.0 g) (H. Noguchi, T. Aoyama, T. Shioiri, *Heterocycles* 2002, 58, 471-504) and PPh$_3$ (18.3 g) in THF (250 ml) was added diethyl azodicarboxylate (12.1 g). After 5 min a solution of diphenylphosphoryl azide (19.2 g) in THF (250 ml) was slowly added from a dropping funnel. The reaction mixture was stirred 6 h at −10° C. and stirring was continued over night at RT. After dilution with Et$_2$O the mixture was washed with H$_2$O. The aqueous layer was washed with one more portion of Et$_2$O. The combined organic layers were dried over Na$_2$SO$_4$ and the solvent was evaporated. Chromatography (silica, CH$_2$Cl$_2$ to CH$_2$Cl$_2$/5% MeOH) afforded 12.0 g (quant.) of product still contaminated by side products. This material was used as this in the following step. Light yellow semisolid.

1.2 {cis-4-[4-(Pyrrolidine-1-carbonyl)-[1,2,3]triazol-1-yl]-cyclohexyl}-carbamic acid tert-butyl ester To a THF (30 ml) solution under $N_2$ of.(cis-4-azido-cyclohexyl)carbamic acid tert-butyl ester (1.50 g) and 1-pyrrolidin-1-yl-propynone (0.769 g) (C. B. Kanner, U. K. Pandit, *Tetrahedron* 1982, 38, 24, 3597-3604) were added CuI (1.19 g) and DIPEA (1.59 ml). The resulting green slurry was stirred 18 h at RT. After dilution with EtOAc (300 ml) the mixture was washed with sat. aq. $NH_4Cl$ (3 x), 1 N HCl (2 x), $H_2O$ and brine. After drying ($MgSO_4$) the solvent was evaporated and the product was purified by chromatography (silica, heptane to EtOAc) to yield 1.14 g (50%) of white crystals. MS 364.2 (100, $[M+H]^+$).

1.3 [1-(cis-4-Amino-cyclohexyl)-1H-[1,2,3]-triazol-4-yl]-pyrrolidin-1-yl-methanone hydrochloride {cis-4-[4-(Pyrrolidine-1-carbonyl)-[1,2,3]triazol-1-yl]-cyclohexyl}-carbamic acid tert-butyl ester (406 mg) was stirred 1 h in a mixture of 4.6 M HCl in EtOAc (3.6 ml) and MeOH (0.84 ml). The solvent was evaporated to yield the product (335 mg, quant.) as white foam after drying on the high vacuum. MS 264.3 (100, $[M+H]^+$).

1.4 2-(2-Chloro-6-fluoro-phenyl)-N-{cis-4-[4-(pyrrolidine-1-carbonyl)-[1,2,3]triazol-1-yl]-cyclohexyl}-acetamide To a solution under $N_2$ of[1-(cis-4-amino-cyclohexyl)-1H-[1,2,3]triazol-4-yl]-pyrrolidin-1-yl-methanone hydrochloride (100 mg) in DMF (4 ml) were added 2-chloro-6-phenylacetic acid (63 mg), TBTU (118 mg) and DIPEA (0.28 ml). The clear solution was stirred 2 h at RT before partitioning it between EtOAc and $H_2O$. The organic phase was dried over $MgSO_4$ and the solvent was evaporated. Chromatography (amino modified silica, $CH_2Cl_2$/MeOH/ 25% $NH_4OH$ 99:9:0.1) afforded the product (93 mg, 64%). Off-white crystals. MS 434.5 (100, $[M+H]^+$).

EXAMPLES 2-18

Examples 2-18 were prepared in analogy to example 1.

| No. | Name | Appearance | MS $[M + H]^+$ |
|---|---|---|---|
| 2 | 3'-Methyl-biphenyl-3-carboxylic acid {cis-4-[4-(pyrrolidine-1-carbonyl)-[1,2,3]triazol-1-yl]-cyclohexyl}-amide from [1-(cis-4-amino-cyclohexyl)-1H-[1,2,3]triazol-4-yl]-pyrrolidin-1-yl-methanone hydrochloride and 3'-methyl-biphenyl-3-carboxylic acid | Orange oil | 458.3 |
| 3 | 4'-Fluoro-biphenyl-3-carboxylic acid {cis-4-[4-(pyrrolidine-1-carbonyl)-[1,2,3]triazol-1-yl]-cyclohexyl}-amide from [1-(cis-4-amino-cyclohexyl)-1H-[1,2,3]triazol-4-yl]-pyrrolidin-1-yl-methanone hydrochloride and 4'-fluoro-biphenyl-3-carboxylic acid | Off-white solid | 462.3 |
| 4 | 2-(4-Chloro-2-methyl-phenoxy)-N-{cis-4-[4-(pyrrolidine-1-carbonyl)-[1,2,3]triazol-1-yl]-cyclohexyl}-propionamide from [1-(cis-4-amino-cyclohexyl)-1H-[1,2,3]triazol-4-yl]-pyrrolidin-1-yl-methanone hydrochloride and 2-(4-chloro-2-methyl-phenoxy)-propionic acid | Off-white solid | 460.3 |
| 5 | 2-Benzo[1,3]dioxol-5-yl-N-{cis-4-[4-(pyrrolidine-1-carbonyl)-[1,2,3]triazol-1-yl]-cyclohexyl}-acetamide from [1-(cis-4-amino-cyclohexyl)-1H-[1,2,3]triazol-4-yl]-pyrrolidin-1-yl-methanone hydrochloride and benzo[1,3]dioxol-5-yl-acetic acid | Colorless oil | 426.4 |
| 6 | 2-Methoxy-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 2-methoxy-benzoic acid | White crystals | 398.4 |
| 7 | 3,4-Dimethoxy-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 3,4-dimethoxy-benzoic acid | White crystals | 428.7 |
| 8 | 4-Methoxy-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 4-methoxy-benzoic acid | White crystals | 398.4 |
| 9 | 4-Chloro-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 4-chloro-benzoic acid | Off-white powder | 402.6 |
| 10 | 3-Chloro-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 3-chloro-benzoic acid | Off-white powder | 402.6 |
| 11 | 3-Fluoro-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 3-fluoro-benzoic acid | Off-white powder | 386.5 |
| 12 | 2-Fluoro-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 2-fluoro-benzoic acid | Off-white powder | 386.4 |

| No. | Name | Appearance | MS [M + H]+ |
|---|---|---|---|
| 13 | 2-Chloro-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 2-chloro-benzoic acid | Off-white poder | 402.6 |
| 14 | 4-Fluoro-N-{cis-4-[4-(pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and 4-fluoro-benzoic acid | Off-white powder | 386.4 |
| 15 | N-{cis-4-[4-(Pyrrolidine-1-carbonyl)-[1,2,3]triazol-1-yl]-cyclohexyl}-benzamide from [1-(cis-4-amino-cyclohexyl)-1H-[1,2,3]triazol-4-yl]-pyrrolidin-1-yl-methanone hydrochloride and benzoic acid | Off-white crystals | 368.1 |
| 16 | Benzo[1,3]dioxole-5-carboxylic acid {cis-4-[4-(pyrrolidine-1-carbonyl)-[1,2,3]triazol-1-yl]-cyclohexyl}-amide from [1-(cis-4-amino-cyclohexyl)-1H-[1,2,3]triazol-4-yl]-pyrrolidin-1-yl-methanone hydrochloride and benzo[1,3]dioxole-5-carboxylic acid | Pink crystals | 412.2 |
| 17 | 1-(2-Chloro-6-fluoro-phenyl)-cyclopentanecarboxylic acid {cis-4-[4-(pyrrolidine-1-carbonyl)-[1,2,3]triazol-1-yl]-cyclohexyl}-amide from [1-(cis-4-amino-cyclohexyl)-1H-[1,2,3]triazol-4-yl]-pyrrolidin-1-yl-methanone hydrochloride and 1-(2-chloro-6-fluoro-phenyl)-cyclopentanecarboxylic acid | Light yellow foam | 488.2 |
| 18 | N-{cis-4-[4-(Pyrrolidine-1-carbonyl)-[1,2,3]triazol-1-yl]-cyclohexyl}-6-trifluoromethyl-nicotinamide from [1-(cis-4-amino-cyclohexyl)-1H-[1,2,3]triazol-4-yl]-pyrrolidin-1-yl-methanone hydrochloride and 6-trifluoromethyl-nicotinic acid | Pink crystals | 437.2 |

EXAMPLE 19

1-{cis-4-[2-(2-Chloro-6-fluoro-phenyl)-acetylamino]-cyclohexyl}-1H-[1,2,3]triazole-4-carboxylic acid phenylamide

19.1 1-(cis-4-tert-Butoxycarbonylamino-cyclohexyl)-1H-[1,2,3]triazole-4-carboxylic acid methyl ester To a THF (30 ml) solution under Ar of (cis-4-azido-cyclohexyl)carbamic acid tert-butyl ester (3.00 g) and propiolic acid methyl ester (1.05 g) were added CuI (2.38 g) and DIPEA (3.18 ml). The resulting slurry was stirred at RT over night. After dilution with EtOAc (200 ml) the mixture was washed with H$_2$O (200 ml), dried over Na$_2$SO$_4$ and the solvent was evaporated. Chromatography (silica, CH$_2$Cl$_2$/MeOH 95:5) yielded 2.63 g (65%) of product. White crystals. MS 325.4 (95, [M+H]+), 269.4 (100, [M−tBu]·+).

19.2 1-(cis-4-Amino-cyclohexyl)-1H-[1,2,3]triazole-4-carboxylic acid methyl ester dihydrochloride A solution of 1-(cis-4-tert-butoxycarbonylamino-cyclohexyl)-1H-[1,2,3]triazole-4-carboxylic acid methyl ester (2.53 g) in a mixture of 4.6 M HCl in EtOAc (25 ml) and MeOH (7.6 ml) was stirred 1 h at RT. The product precipitated and was collected by filtration. Yield: 1.36 g (58%). White powder. MS 225.0 (100, [M+H]+).

19.3 1-{cis-4-[2-(2-Chloro-6-fluoro-phenyl)-acetylamino]-cyclohexyl}-1H-[1,2,3]triazole-4-carboxylic acid methyl ester The title compound was prepared from 1-{cis-4-amino-cyclohexyl)-1H-[1,2,3]triazole-4-carboxylic acid methyl ester} hydrochloride (1.35 g) in analogy to example 1. Yield: 1.45 g (71%). Light brownish crystals. MS 395.1 (69, [M+H]+), 412.1 (100, [M+NH$_4$]+).

19.4 1-{cis-4-[2-(2-Chloro-6-fluoro-phenyl)-acetylamino]-cyclohexyl}-1H-[1,2,3]triazole-4-carboxylic acid phenylamide A solution under N$_2$ of aniline (35 mg) in CH$_2$Cl$_2$ (1 ml) was cooled to 0° C. and a 2 M solution of Me$_3$Al in Tol (0.19 ml) was cautiously added. The cooling bath was removed and the solution was stirred 30 min at RT. After cooling again to 0° C., 1-{cis-4-[2-(2-chloro-6-fluoro-phenyl)-acetylamino]-cyclohexyl}-1H-[1,2,3]triazole-4-carboxylic acid methyl ester (100 mg) in CH$_2$Cl$_2$ (1 ml) was added. The reaction mixture was stirred over night at RT, then it was carefully poured on 1 M HCl (5 ml) and the product was extracted with CH$_2$Cl$_2$ (5 ml). The organic layer was washed with H$_2$O (5 ml) and dried (Na$_2$SO$_4$). The solvent was evaporated to yield 115 mg (99%) of product as light yellowish crystals. MS 456.2 (100, [M+H]+).

EXAMPLE 20

1-{cis-4-[2-(2-Chloro-6-fluoro-phenyl)-acetylamino]-cyclohexyl}-1H-[1,2,3]triazole-4-carboxylic acid cyclopentylamide The title compound was prepared in analogy to example 19. Brown powder. MS 448.1 (76, [M+H]+), 465.2 (100, [M+NH$_4$]+).

EXAMPLE 21

2-(2-Chloro-6-fluoro-phenyl)-N-{cis-4-[4-(piperidine-1-carbonyl)-[1,2,3]triazol-1-yl]-cyclohexyl}-acetamide

21.1 1-{cis-4-[2-(2-Chloro-6-fluoro-phenyl)-acetylamino]-cyclohexyl}-1H-[1,2,3]triazol-4-carboxylic acid 1-{cis-4-[2-(2-Chloro-6-fluoro-phenyl)-acetylamino]-cyclohexyl}-1H-[1,2,3]triazole-4-carboxylic acid methyl ester (400 mg) was dissolved in a mixture of THF (3.2 ml)/MeOH (3.2 ml)/H$_2$O (1.6 ml) and LiOH.H$_2$O (43 mg) was added. The reaction mixture was stirred 1 h at 60° C., then it was poured on a mixture of H$_2$O (35 ml) and EtOAc (35 ml). The aqueous layer was collected, acidified with 1 M HCl to pH<4 and extracted with EtOAc (2×35 ml). After drying over Na$_2$SO$_4$ the solvent was evaporated to yield 341 mg (88%) of product. White powder. MS 379.1 (100, [M−H]$^-$).

21.2 2-(2-Chloro-6-fluoro-phenyl)-N-{cis-4-[4-(piperidine-1-carbonyl)-[1,2,3]triazol-1-yl]-cyclohexyl}-acetamide To a solution under Ar of 1-{cis-4-[2-(2-chloro-6-fluoro-phenyl)-acetylamino]-cyclohexyl}-1H-[1,2,3]triazole-4-carboxylic acid (100 mg) in DMF (4 ml) were added piperidine (22 mg), TBTU (93 mg) and DIPEA (0.13 ml). The solution was stirred 1 h at RT before partitioning it between EtOAc (50 ml) and H$_2$O (50 ml). The organic phase was dried over Na$_2$SO$_4$ and the solvent was evaporated. Chromatography (silica, CH$_2$Cl$_2$ to CH$_2$Cl$_2$ 5% MeOH) afforded the product (112 mg, 95%). Off-white solid. MS 448.1 (100, [M+H]$^+$).

EXAMPLE 22

1-{cis-4-[2-(2-Chloro-6-fluoro-phenyl)-acetylamino]-cyclohexyl}-1H-[1,2,3]triazole-4-carboxylic acid diethylamide The title compound was prepared in analogy to example 21. Light brown solid. MS 436.2 (100, [M+H]$^+$).

The invention claimed is:
1. A compound of formula (I)

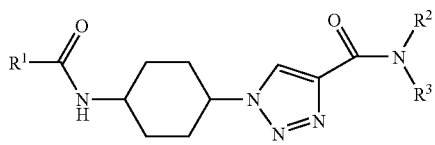

I wherein
R$^1$ is —(CRR')$_n$-aryl, —(CRR')$_n$-heteroaryl, —(CRR')$_n$-O-aryl or —(CRR')$_n$—O-heteroaryl, wherein the aryl or heteroaryl groups are unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen, or is —(CRR')$_n$-2-benzo[1.3]dioxolyl;
R and R' are each independently selected from hydrogen and lower alkyl or are together with the carbon atom to which they are attached a cycloalkyl group;
R$^2$ and R$^3$ are each independently selected from hydrogen, lower alkyl, phenyl and cycloalkyl or together with the N-atom to which they are attached form a five or six membered saturated heterocycle;
n is 0 or 1;
or a pharmaceutically suitable acid addition salt, enantiomer, diastereoisomer, or racemic mixture thereof.

2. A compound of claim 1 wherein R$^1$ is (CRR')$_n$-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

3. A compound of claim 2, wherein R$^1$ is —CH$_2$-phenyl, and the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

4. A compound of claim 3, selected from the group consisting of
2-(2-chloro-6-fluoro-phenyl)-N-{cis-4-[4-(pyrrolidine-1-carbonyl)-[1,2,3]triazol-1-yl]-cyclohexyl}-acetamide,
1-{cis-4-[2-(2-chloro-6-fluoro-phenyl)-acetylamino]-cyclohexyl}-1H-[1,2,3]triazole-4-carboxylic acid phenylamide,
1-{cis-4-[2-(2-chloro-6-fluoro-phenyl)-acetylamino]-cyclohexyl}-1H-[1,2,3]triazole-4-carboxylic acid cyclopentylamide,
2-(2-chloro-6-fluoro-phenyl)-N-{cis-4-[4-(piperidine-1-carbonyl)-[1,2,3]triazol-1-yl]-cyclohexyl}-acetamide and
1-{cis-4-[2-(2-chloro-6-fluoro-phenyl)-acetylamino]-cyclohexyl}-1H-[1,2,3]triazole-4-carboxylic acid diethylamide.

5. A compound of claim 2, wherein R$^1$ is phenyl, and the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

6. A compound of claim 5, selected from the group consisting of
3'-methyl-biphenyl-3-carboxylic acid {cis-4-[4-(pyrrolidine-1-carbonyl)-[1,2,3]triazol-1-yl]-cyclohexyl}-amide,
4'-fluoro-biphenyl-3-carboxylic acid {cis-4-[4-(pyrrolidine-1-carbonyl)-[1,2,3]triazol-1-yl]-cyclohexyl}-amide,
2-methoxy-N-{cis-4-[4-(pyrrolidine-1-carbonyl)-[1,2,3]triazol-1-yl]-cyclohexyl}-benzamide,
3,4-dimethoxy-N-{cis-4-[4-(pyrrolidine-1-carbonyl)-[1,2,3]triazol-1-yl]-cyclohexyl}-benzamide,
4-methoxy-N-{cis-4-[4-(pyrrolidine-1-carbonyl)-[1,2,3]triazol-1-yl]-cyclohexyl}-benzamide,
4-chloro-N-{cis-4-[4-(pyrrolidine-1-carbonyl)-[1,2,3]triazol-1-yl]-cyclohexyl}-benzamide,
3-chloro-N-{cis-4-[4-(pyrrolidine-1-carbonyl)-[1,2,3]triazol-1-yl]-cyclohexyl}-benzamide,
3-fluoro-N-{cis-4-[4-(pyrrolidine-1-carbonyl)-[1,2,3]triazol-1-yl]-cyclohexyl}-benzamide,
2-fluoro-N-{cis-4-[4-(pyrrolidine-1-carbonyl)-[1,2,3]triazol-1-yl]-cyclohexyl}-benzamide,
2-chloro-N-{cis-4-[4-(pyrrolidine-1-carbonyl)-[1,2,3]triazol-1-yl]-cyclohexyl}-benzamide,
4-fluoro-N-{cis-4-[4-(pyrrolidine-1-carbonyl)-[1,2,3]triazol-1-yl]-cyclohexyl}-benzamide and
N-{cis-4-[4-(pyrrolidine-1-carbonyl)-[1,2,3]triazol-1-yl]-cyclohexyl}-benzamide.

7. A compound of claim 2, wherein R$^2$ and R$^3$ are each independently hydrogen or lower alkyl.

8. A compound of claim 2, wherein at least one of R$^2$ and R$^3$ is cycloalkyl.

9. A compound of claim 2, wherein at least one of R$^2$ and R$^3$ is phenyl.

10. A compound of claim 2, wherein $R^2$ and $R^3$ together with the N-atom to which they are attached form a five or six membered saturated heterocycle.

11. A compound of claim 1, wherein $R^1$ is $(CRR')_n$—O-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

12. A compound of claim 11, wherein $R^1$ is —CH(CH$_3$)—O-phenyl, wherein the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

13. A compound of claim 12, wherein the compound is 2-(4-chloro-2-methyl-phenoxy)-N-{cis-4-[4-(pyrrolidine-1-carbonyl)-[1,2,3]triazol-1-yl]-cyclohexyl}-propionamide.

14. A compound of claim 11, wherein $R^2$ and $R^3$ are each independently hydrogen or lower alkyl.

15. A compound of claim 11, wherein at least one of $R^2$ and $R^3$ is cycloalkyl.

16. A compound of claim 11, wherein at least one of $R^2$ and $R^3$ is phenyl.

17. A compound of claim 11, wherein $R^2$ and $R^3$ together with the N-atom to which they are attached form a five or six membered saturated heterocycle.

18. A compound of claim 1, wherein $R^1$ is $(CRR')_n$-2-benzo[1.3]dioxolyl.

19. A compound of claim 18, wherein $R^1$ is —CH$_2$-2-benzo[1.3]dioxolyl.

20. A compound of claim 19, wherein the compound is 2-benzo[1,3]dioxol-5-yl-N-{cis-4-[4-(pyrrolidine-1-carbonyl)-[1,2,3]triazol-1-yl]-cyclohexyl}-acetamide.

21. A compound of claim 18, wherein $R^1$ is 2-benzo[1.3]dioxolyl.

22. A compound of claim 21, wherein the compound is benzo[1,3]dioxole-5-carboxylic acid {cis-4-[4-(pyrrolidine-1-carbonyl)-[1,2,3]triazol-1-yl]-cyclohexyl}-amide.

23. A compound of claim 18, wherein $R^2$ and $R^3$ are each independently hydrogen or lower alkyl.

24. A compound of claim 18, wherein at least one of $R^2$ and $R^3$ is cycloalkyl.

25. A compound of claim 18, wherein at least one of $R^2$ and $R^3$ is phenyl.

26. A compound of claim 18, wherein $R^2$ and $R^3$ together with the N-atom to which they are attached form a five or six membered saturated heterocycle.

27. A compound of claim 1, wherein $R^1$ is $(CRR')_n$-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

28. A compound of claim 1, wherein $R^1$ is pyridinyl.

29. A compound of claim 28, wherein the compound is N-{cis-4-[4-(pyrrolidine-1-carbonyl)-[1,2,3]triazol-1-yl]-cyclohexyl}-6-trifluoromethyl-nicotinamide.

30. A compound of claim 27, wherein $R^2$ and $R^3$ are each independently hydrogen or lower alkyl.

31. A compound of claim 27, wherein at least one of $R^2$ and $R^3$ is cycloalkyl.

32. A compound of claim 27, wherein at least one of $R^2$ and $R^3$ is phenyl.

33. A compound of claim 27, wherein $R^2$ and $R^3$ together with the N-atom to which they are attached form a five or six membered saturated heterocycle.

34. A compound of claim 2, wherein $R^1$ is —C(R,R')-phenyl, and the phenyl ring is unsubstituted or substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen and R and R' are together with the carbon atom to which they are attached a cycloalkyl group.

35. A compound of claim 34, wherein the compound is 1-(2-chloro-6-fluoro-phenyl)-cyclopentanecarboxylic acid {cis-4-[4-(pyrrolidine-1-carbonyl)-[1,2,3]triazol-1-yl]-cyclohexyl}-amide.

36. A compound of claim 1, wherein $R^1$ is $(CRR')_n$—O-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

37. A compound of claim 36, wherein $R^2$ and $R^3$ are each independently hydrogen or lower alkyl.

38. A compound of claim 36, wherein at least one of $R^2$ and $R^3$ is cycloalkyl.

39. A compound of claim 36, wherein at least one of $R^2$ and $R^3$ is phenyl.

40. A compound of claim 36, wherein $R^2$ and $R^3$ together with the N-atom to which they are attached form a five or six membered saturated heterocycle.

41. A compound of claim 1, wherein $R^2$ and $R^3$ together with the N-atom to which they are attached form a five or six membered saturated heterocycle.

42. A compound of claim 41, wherein $R^2$ and $R^3$ together with the N-atom to which they are attached form a pyrrolidine or piperidine ring.

43. A compound of claim 42, wherein $R^1$ is $(CRR')_n$-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

44. A compound of claim 42, wherein $R^1$ is $(CRR')_n$-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

45. A compound of claim 42, wherein $R^1$ is $(CRR')_n$—O-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

46. A compound of claim 42, wherein $R^1$ is $(CRR')_n$—O-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

47. A compound of claim 1, wherein $R^3$ is phenyl.

48. A compound of claim 47, wherein $R^1$ is $(CRR')_n$-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

49. A compound of claim 47, wherein $R^1$ is $(CRR')_n$-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

50. A compound of claim 47, wherein $R^1$ is $(CRR')_n$—O-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

51. A compound of claim 47, wherein $R^1$ is $(CRR')_n$—O-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

52. A compound of claim 1, wherein $R^3$ is cycloalkyl.

53. A compound of claim 52, wherein $R^1$ is $(CRR')_n$-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

54. A compound of claim 52, wherein $R^1$ is $(CRR')_n$-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

55. A compound of claim 52, wherein $R^1$ is $(CRR')_n$—O-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

56. A compound of claim 52, wherein $R_1$ is $(CRR')_n$—O-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

57. A compound of claim 1, wherein $R^2$ and $R^3$ are each independently lower alkyl.

58. A compound of claim 57, wherein $R^1$ is $(CRR')_n$-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

59. A compound of claim 57, wherein $R^1$ is $(CRR')_n$-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

60. A compound of claim 57, wherein $R^1$ is $(CRR')_n$—O-aryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

61. A compound of claim 57, wherein $R^1$ is $(CRR')_n$—O-heteroaryl optionally substituted by one or two substituents selected from the group consisting of halogen, lower alkyl, lower alkoxy, and lower alkyl substituted by halogen, or is unsubstituted or substituted phenyl, wherein the substitution on the phenyl group is lower alkyl or halogen.

62. A compound of claim 1, wherein $R^2$ and $R^3$ are each independently from hydrogen, lower alkyl, phenyl or cycloalkyl.

* * * * *